United States Patent [19]

Okorodudu

[11] 4,101,432
[45] Jul. 18, 1978

[54] LUBRICANT COMPOSITIONS CONTAINING ORGANOPHOSPHORUS DERIVATIVES OF HYDROXYCARBOXYLIC ACIDS

[75] Inventor: Abraham O. M. Okorodudu, West Deptford, N.J.

[73] Assignee: Mobil Oil Corporation, New York, N.Y.

[21] Appl. No.: 815,630

[22] Filed: Jul. 14, 1977

[51] Int. Cl.$^2$ ............................................. C10M 1/10
[52] U.S. Cl. ................................. 252/49.8; 260/941; 260/942
[58] Field of Search ............... 252/49.8; 260/941, 942

[56] References Cited

U.S. PATENT DOCUMENTS

| | | | |
|---|---|---|---|
| 2,251,953 | 8/1941 | Prutton et al. | 252/49.8 X |
| 2,252,675 | 8/1941 | Prutton et al. | 252/49.8 X |
| 2,894,014 | 7/1959 | Stiles et al. | 260/941 |
| 3,093,672 | 6/1963 | Miller | 252/49.8 X |
| 4,005,159 | 1/1977 | Koch et al. | 252/49.8 X |

*Primary Examiner*—Delbert E. Gantz
*Assistant Examiner*—Andrew H. Metz
*Attorney, Agent, or Firm*—Charles A. Huggett; Raymond W. Barclay; Howard M. Flournoy

[57] ABSTRACT

Certain organophosphorus derivatives of hydroxycarboxylic acids provide excellent load-carrying protection for hydrocarbon compositions when incorporated therein and are novel compounds.

28 Claims, No Drawings

LUBRICANT COMPOSITIONS CONTAINING ORGANOPHOSPHORUS DERIVATIVES OF HYDROXYCARBOXYLIC ACIDS

BACKGROUND OF THE INVENTION

1. Field of the Invention

This application is directed to lubricant compositions comprising oils of lubricant viscosity or greases prepared therefrom containing a minor amount, sufficient to improve the load-carrying properties thereof, of organophosphorus derivatives of alkyl or aryl hydroxycarboxylic acids, and to said organophosphorus derivatives.

2. Description of the Prior Art

The use of phosphorus compounds, per se, as load-carrying or EP agents in lubricant compositions is well known. The use of organic phosphorus compounds in combination with, for example, hindered phenols to produce load-carrying additives for lubricants in known from U.S. Pat. Nos. 3,115,465; and 3,986,967 discloses organophosphorus derivatives of benzotriazole with the ability to support higher load factors. So far as is known, however, no art exists which suggests the herein disclosed reaction products of certain hydroxycarboxylic acids and organophosphorus compounds, or use thereof as load-carrying agents.

SUMMARY OF THE INVENTION

The application is directed to lubricant compositions having a major amount of a lubricant, e.g., an oil of lubricating viscosity or a grease prepared therefrom and a minor load-carrying amount of the hereinbelow described compounds.

The invention further provides for compounds having the following general formula:

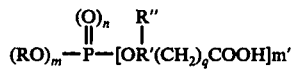

wherein R is alkyl of 1 to 32 carbon atoms, aryl or alkaryl and R' is alkylene or arylene and R" is H, alkyl of 1 to 30 carbon atoms, aryl or alkaryl and where $n$ is zero or 1 and $q$ is zero or 1 to 30 and $m$ and $m'$ are 1 or 2 with the proviso that the sum of $m$ and $m'$ equals 3.

DESCRIPTION OF SPECIFIC EMBODIMENTS

Although the compounds of the invenion may be prepared in sereral ways, they are preferably prepared as described below by reacting an organophosphorus halide and a hydroxycarboxylic acid.

Suitable organophosphorus halides include compounds having the following general formula:

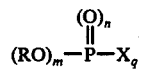

which includes such halides as $ROPX_2$, $(RO)_2PX$, $(RO)_2P(O)X$ and $ROP(O)X_2$, where R is alkyl of 1 to 32 carbon atoms, aryl or alkaryl, X is chloro-, bromo- or iodo-, $m$ is 1 to 2, $n$ is zero or 1, and $q$ is 1 or 2, the sum of $m$ and $q$ being 3. Preferred are those halides having the structure $(RO)_2$—$P(O)Cl$ or $(RO)_2PCl$.

Suitable hydroxy carboxylic acids include compounds having the following general structure:

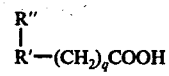

where R' is alkeylene or arylene and R" is H, alkyl of 1 to 30 carbon atoms and $q$ is zero or 1 to 30. Preferred is lactic or 12-hydroxy stearic acid.

The organophosphorus halide, e.g., $ROPCl_2$, $(RO)_2$—P—Cl and $(RO)_2$—P(O)Cl, may be conveniently reacted with hydroxy carboxylic acid in the following manner:

(1) 12-hydroxy stearic acid

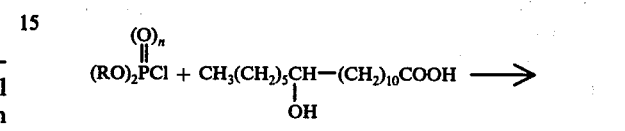

(2) Lactic acid

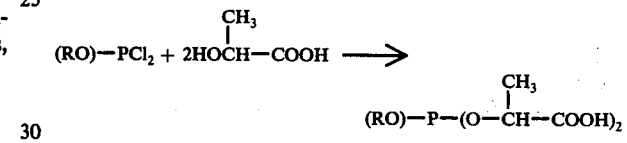

As has already been stated, the R group in the organophosphorus reactants are hydrocarbyl containing up to 32 carbon atoms, which can be alkyl, aromatic or alkyl-substituted aromatic. The aromatic groups include phenyl, naphthyl and anthryl, and those members substituted with a $C_1$-$C_{18}$ alkyl. Such alkyl groups include methyl, butyl, octyl, decyl, dodecyl, tetradecyl, octadecyl and the like, and it will be understood that the mention of each of these is a disclosure of its attachment to each of the aromatic groups mentioned and the incorporation of the alkylaromatic compound into the various final products contemplated by this invention. Finally, the alkyl group R can also have from 1 to 32 carbon atoms and includes methyl, ethyl, hexyl, nonyl, tetradecyl and octadecyl, eicosyl, pentacosyl, triacontyl and dotriacontyl. Here again, the disclosure of each of these groups is a disclosure of their incorporation in all the various final products of this invention.

The compounds of this invention are especially effective in lubricant compositions in which the lubricant base is a petroleum product, such as a mineral lubricating oil, or a synthetic fluid. Such synthetic fluids include synthetic hydrocarbon oils derived from long chain alkanes or olefin polymers, ester oils obtained from polyhydric alcohols and monocarboxylic acids or monohydric alcohols and polycarboxylic acids. Also the lubricants herein include greases made from the named classes of lubricant compositions and/or fluids.

The concentration of additive may vary from about 0.05 to about 10% by weight. Optimum performance characteristics are evidenced by lubricants containing from about 0.25% to about 2% by weight of the additives of this invention, and this is the preferred range of concentration.

Having defined the invention in general terms, the following Examples are offered as illustrations.

EXAMPLE 1

Preparation of

Benzene (200 ml) and lactic acid (3 mols) were charged into a suitable reaction vessel protected from moisture. While stirring under $N_2$ purge, 0.5 mol octadecyl phosphorodichloridite was added rapidly. Following the exothermic reaction, the mixture was heated at reflux for 2 hours, during which there was HCl evolution. After cooling, the excess lactic acid was separated and the residue stripped under vacuum. The final product had about 3.1% phosphorus.

EXAMPLE 2

Preparation of

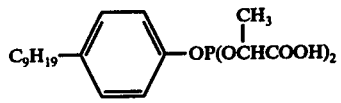

This compound was prepared as outlined in Example 1, except that nonylphenyl phosphorodichloridite was used. The final product had about 4.2% phosphorus.

EXAMPLE 3

Preparation of

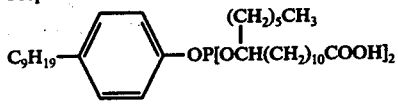

This compound was prepared as outlined in Example 1, except that nonylphenyl phosphorodichloridite and 12-hydroxyoctadecanoic acid were the reactants and bis(2-methoxyethyl) ether was used as solvent.

EXAMPLE 4

Preparation of:

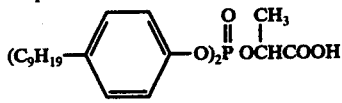

Bis(2-methoxyethyl)ether (250 ml) and lactic acid (2 mols) were charged into a reaction flask protected from moisture. To this mixture, while stirring under $N_2$ purge was added about 0.5 mol di(nonylphenyl)phosphorochloridate dropwise. Following the addition, the reaction mixture was refluxed for 18 hours, and then stripped of excess lactic acid and solvent under vacuum. The final product obtained had 4.3% phosphorus.

EXAMPLE 5

Preparation of:

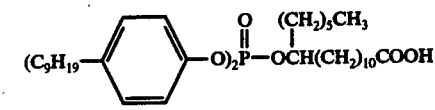

This compound was prepared as outlined in Example 4, except that 12-hydroxyoctadecanoic acid was used. The product obtained had 2.5% phosphorus.

EXAMPLE 6

Preparation of:

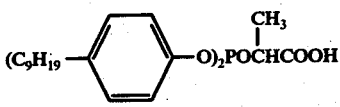

This compound was prepared as outlined in Example 4 except that di(nonylphenyl) phosphorochloridite was used.

EXAMPLE 7

Preparation of:

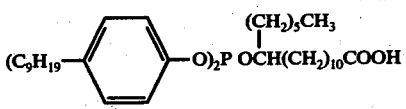

This compound was prepared as outlined in Example 4 except that 12-hydroxyoctadecanoic acid and di(nonylphenyl) phosphorochloridite were used. The product had 3.5% phosphorus.

EXAMPLE 8

Preparation of:

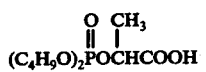

This compound was prepared as outlined in Example 4 except that dibutyl phosphorochloridate was used. The product had 8.4% phosphorus.

EXAMPLE 9

Preparation of:

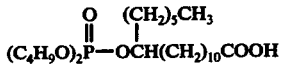

This compound was prepared as outlined in Example 4 except that dibutyl phosphorochloridate and 12-hydroxyoctadecanoic acid were used as the reactants. The final product had 7.7% phosphorus.

EXAMPLE 10

Preparation of:

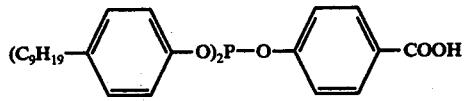

p-hydroxybenzoic acid (0.25 mol) and 150 ml of bis(2-methoxyethyl) ether were charged into a reaction flask protected from moisture and stirred under $N_2$ purge. To this was added 0.25 mol di(nonylphenyl) phosphorochloridite, dropwise. Following the exothermic reaction, the mixture was refluxed for 6 hours and stripped under vacuum to give a product containing 4.6% phosphorus.

EXAMPLE 11

Preparation of:

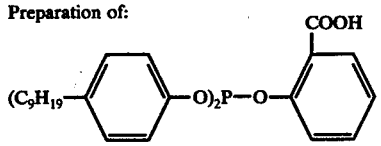

This compound was prepared as outlined in Example 10 except that salicyclic acid was used. The product contained 4.8% phosphorus.

The additives described hereinabove were evaluated in the standard 4-Ball Wear Test using ½ in. 52100 Steel Balls at a load of 60 Kg and for 30 minutes under the conditions set forth in Table I and II below. The oils used were a 80/20 mixture of a solvent refined Mid-Continent paraffinic 150/160 second bright mineral oil and a 200/210 second refined Mid-Continent neutral mineral oil (Table I), and a synthetic ester lubricant made by reacting pentaerythritol with an equimolar mixture of $C_5$ and $C_9$ monocarboxylic acids (Table II).

TABLE I

| Ex. | Additive | Conc. Wt. % | Temp °F | Scar Diameter (mm) (RPM) | | | |
|---|---|---|---|---|---|---|---|
| | | | | 500 | 1,000 | 1,500 | 2,000 |
| | Mineral Oil Base Stock | 100 | Room | 0.50 | 0.60 | 0.88 | 2.34 |
| | | | 200 | 0.60 | 1.06 | 1.86 | 2.23 |
| | | | 390 | 1.0 | 1.31 | 2.06 | — |
| 1 | $C_{18}H_{37}OP(OCHCOOH)_2$ with $CH_3$ | 1 | Room | 0.50 | 0.40 | 0.50 | 0.60 |
| | | | 200 | 0.50 | 0.50 | 0.50 | 0.70 |
| | | | 390 | 0.50 | 0.60 | 0.60 | 0.70 |
| 2 | $C_9H_{19}$-⌬-$OP(OCHCOOH)_2$ with $CH_3$ | 1 | Room | — | — | — | — |
| | | | 200 | 0.50 | 0.60 | 0.60 | 0.60 |
| | | | 390 | 0.50 | 0.80 | 0.80 | 0.90 |
| 3 | $C_9H_{19}$-⌬-$OP[OCH(CH_2)_{10}COOH]_2$ with $(CH_2)_5CH_3$ | 1 | Room | 0.40 | 0.40 | 0.50 | 0.60 |
| | | | 200 | 0.40 | 0.50 | 0.60 | 0.60 |
| | | | 390 | 0.50 | 0.60 | 0.70 | 0.70 |
| 4 | $(C_9H_{19}$-⌬-$O)_2P\overset{O}{\parallel}OCHCOOH$ with $CH_3$ | 1 | Room | 0.50 | 0.40 | 0.40 | 0.50 |
| | | | 200 | 0.50 | 0.40 | 0.50 | 0.60 |
| | | | 390 | 0.50 | 1.05 | 0.70 | 0.70 |
| 5 | $(C_9H_{19}$-⌬-$O)_2P\overset{O}{\parallel}—OCH(CH_2)_{10}COOH$ with $(CH_2)_5CH_3$ | 1 | Room | 0.50 | 0.50 | 0.50 | 0.50 |
| | | | 200 | 0.50 | 0.50 | 0.50 | 0.60 |
| | | | 390 | 0.50 | 0.50 | 0.70 | 0.90 |
| 6 | $(C_9H_{19}$-⌬-$O)_2POCHCOOH$ with $CH_3$ | 1 | Room | 0.50 | 0.50 | 0.50 | 0.60 |
| | | | 200 | 0.50 | 0.50 | 0.60 | 0.60 |
| | | | 390 | 0.50 | 0.70 | 0.80 | 0.70 |
| 7 | $(C_9H_{19}$-⌬-$O)_2P\ OCH(CH_2)_{10}COOH$ with $(CH_2)_5CH_3$ | 1 | Room | 0.40 | 0.50 | 0.50 | 0.60 |
| | | | 200 | 0.40 | 0.50 | 0.50 | 0.50 |
| | | | 390 | 0.50 | 0.60 | 1.00 | 1.20 |
| 8 | $(C_4H_9O)_2POCHCOOH$ with $\overset{O}{\parallel}$ and $CH_3$ | 1 | Room | 0.50 | 0.60 | 0.80 | 0.90 |
| | | | 200 | 0.70 | 0.70 | 1.00 | 1.20 |
| | | | 390 | 0.70 | 0.80 | 0.90 | 1.00 |
| 9 | $(C_4H_9O)_2P\overset{O}{\parallel}—OCH—(CH_2)_{10}COOH$ with $(CH_2)_5CH_3$ | 1 | Room | 0.40 | 0.50 | 0.80 | 0.60 |
| | | | 200 | 0.50 | 0.50 | 0.60 | 0.60 |
| | | | 390 | 0.60 | 0.60 | 0.60 | 0.60 |
| 10 | $(C_9H_{19}$-⌬-$O)_2P$-$O$-⌬-$COOH$ | 1 | Room | 0.40 | 0.50 | 0.50 | 0.53 |
| | | | 200 | 0.50 | 0.50 | 0.50 | 0.60 |
| | | | 390 | 0.50 | 0.60 | 0.60 | 0.70 |
| 11 | $(C_9H_{19}$-⌬-$O)_2P$-$O$-⌬-$COOH$ (ortho) | 1 | Room | 0.40 | 0.43 | 0.40 | 0.65 |
| | | | 200 | 0.50 | 0.46 | 0.50 | — |
| | | | 390 | 0.50 | 0.60 | 0.65 | 0.70 |

TABLE II

| Example | Additive | Conc. Wt.% | Temp. °F | Scar Diameter (mm) Speed (RPM) | | | |
|---|---|---|---|---|---|---|---|
| | | | | 500 | 1,000 | 1,500 | 2,000 |
| 1 | Synthetic Base Stock | 100 | Room | 0.70 | 0.90 | 0.90 | 1.95 |
| | | | 200 | 0.80 | 0.90 | 2.0 | 2.10 |
| | | | 390 | 0.90 | 1.30 | 1.50 | 2.40 |
| 2 | $C_9H_{19}$-⌬-$OP[OCH(CH_2)_{10}COOH]_2$ with $(CH_2)_5CH_3$ | 1 | Room | 0.50 | 0.50 | 0.50 | 0.60 |
| | | | 200 | 0.40 | 0.50 | 0.60 | 0.70 |
| | | | 390 | 0.65 | 0.80 | 0.90 | 1.85 |
| 3 | $(C_9H_{19}$-⌬-$O)_2POCHCOOH$ with $CH_3$ | 1 | Room | 0.50 | 0.60 | 0.60 | 0.58 |
| | | | 200 | 0.50 | 0.60 | 0.70 | 0.70 |
| | | | 390 | 0.60 | 0.80 | 0.65 | 2.3 |

TABLE II-continued

| Example | Additive | Conc. Wt.% | Temp. °F | Scar Diameter (mm) Speed (RPM) | | | |
|---|---|---|---|---|---|---|---|
| | | | | 500 | 1,000 | 1,500 | 2,000 |
| 4 | 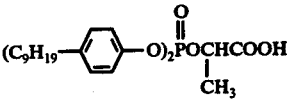 | 1 | Room | 0.50 | 0.80 | 1.86 | 1.95 |
| | | | 200 | 0.60 | 0.80 | 1.80 | 1.95 |
| | | | 390 | 0.80 | 0.90 | 1.90 | 2.0 |

The data in the Tables clearly establish that the lubricant additives in accordance herewith possess good load-carrying properties.

It is understood that only preferred embodiments have been exemplified, which in no way limit the specification or claims, departure therefrom is within the skill of the art.

What is claimed is:

1. A lubricant composition comprising a major amount of an oil of lubricating viscosity or grease prepared therefrom and a minor load-carrying amount of a compound of the formula:

$$(RO)_m - \overset{(O)_n}{\underset{}{P}} - (OR'(CH_2)_q COOH)_{m'}$$
$$\phantom{(RO)_m - P}\overset{R''}{|}$$

where R is alkyl of 1 to 32 carbon atoms, aryl or alkaryl and R' is alkylene or arylene and R" is H, alkyl of 1 to 30 carbon atoms, aryl or alkaryl and where n is zero or 1 and q is zero or 1 to 30 and m and m' are 1 or 2 with the proviso that the sum of m and m' is 3.

2. The composition of claim 1 where the compound is:

3. The composition of claim 1 where the compound is:

4. The composition of claim 1 where the compound is:

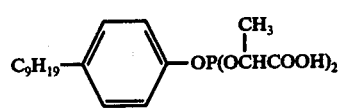

5. The composition of claim 1 where the compound is:

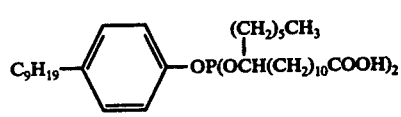

6. The composition of claim 1 where the compound is:

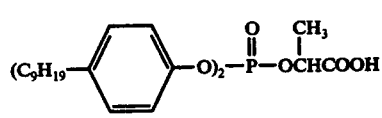

7. The compound of claim 1 where the compound is:

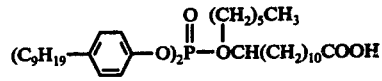

8. The composition of claim 1 where the compound is:

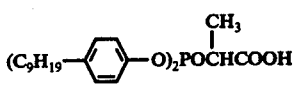

9. The composition of claim 1 where the compound is:

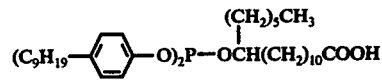

10. The composition of claim 1 where the compound is:

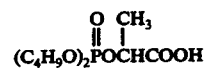

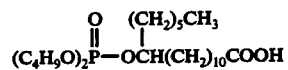

11. The composition of claim 1 where the compound is:

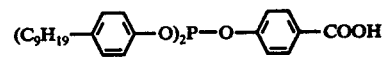

12. The composition of claim 1 where the compound is:

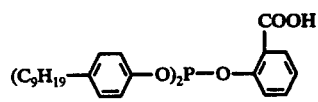

13. The composition of claim 1 where the oil of lubricating viscosity is a mineral oil.

14. The composition of claim 1 where the oil of lubricating viscosity is a synthetic oil.

15. The composition of claim 1 where the amount of said compound therein varies from 0.05–10 wt. % based on the total weight of the composition.

16. The composition of claim 15 where the amount of said compound therein varies from 0.25–2 wt. % based on the total weight of the composition.

17. A compound having the following general formula:

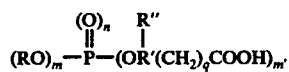

where R is alkyl of 1 to 32 carbon atoms, aryl or alkaryl and R' is alkylene or arylene and R" is H, alkyl of 1 to 30 carbon atoms, aryl or alkaryl and where $n$ is zero or 1 and $q$ is zero or 1 to 30 and $m$ and $m'$ are 1 or 2 and the sum of $m$ and $m'$ equals 3.

18. The compound of claim 17 where the compound is:

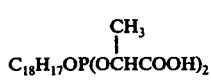

19. The compound of claim 17 where the compound is:

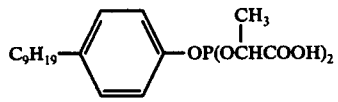

20. The compound of claim 17 where the compound is:

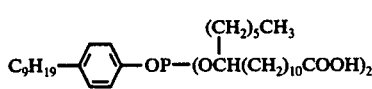

21. The compound of claim 17 where the compound is:

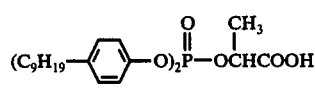

22. The compound of claim 17 where the compound is:

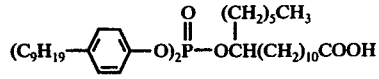

23. The compound of claim 17 where the compound is:

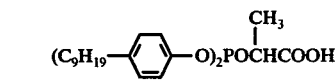

24. The compound of claim 17 where the compound is:

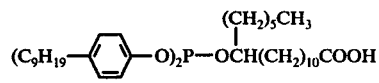

25. The compound of claim 17 where the compound is:

26. The compound of claim 17 where the compound is:

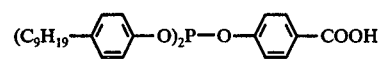

27. The compound of claim 17 where the compound is:

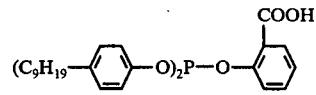

28. The compound of claim 17 where the compound is:

(C₉H₁₉—⌬—O)₂P—O—⌬—COOH with COOH substituent

* * * * *